United States Patent [19]

Garwoli

[11] 4,338,026

[45] Jul. 6, 1982

[54] APPARATUS FOR DETERMINING PROPERTIES OF MATTER

[75] Inventor: Wolfgang N. Garwoli, North Balwyn, Australia

[73] Assignee: The State of Victoria, Victoria, Australia

[21] Appl. No.: 83,108

[22] Filed: Oct. 9, 1979

[30] Foreign Application Priority Data

Oct. 9, 1978 [AU] Australia .............................. PD6290
Oct. 9, 1978 [AU] Australia .............................. PD6291
Oct. 9, 1978 [AU] Australia .............................. PD6292
Oct. 9, 1978 [AU] Australia .............................. PD6293

[51] Int. Cl.³ ...................... G01B 11/04; G01B 11/08
[52] U.S. Cl. .................................... 356/73; 356/383; 356/386; 356/387
[58] Field of Search .......... 356/73, 383, 387, 384–386

[56] References Cited

U.S. PATENT DOCUMENTS 3,299,256 1/1967 Howe et al. .................... 235/92 PC

FOREIGN PATENT DOCUMENTS 371421 5/1973 U.S.S.R. .............................. 356/383

Primary Examiner—Vincent P. McGraw
Attorney, Agent, or Firm—Cushman, Darby & Cushman

[57] ABSTRACT

An apparatus for testing a sample of fibres or filaments including a scanning zone in which said sample is located and scanning means. Transport means is provided for producing relative movement between the scanning zone and the scanning means whereby to define a primary scan path therebetween. The scanning means includes irradiation means arranged to irradiate a portion of the scanning zone, and at least one radiation detector responsive to the irradiation whereby to provide an output indicating the presence or otherwise of a discrete length of fibre or filament in the portion, and processing means for processing the detector output to provide a measure of one or more parameters of the sample.

9 Claims, 7 Drawing Figures

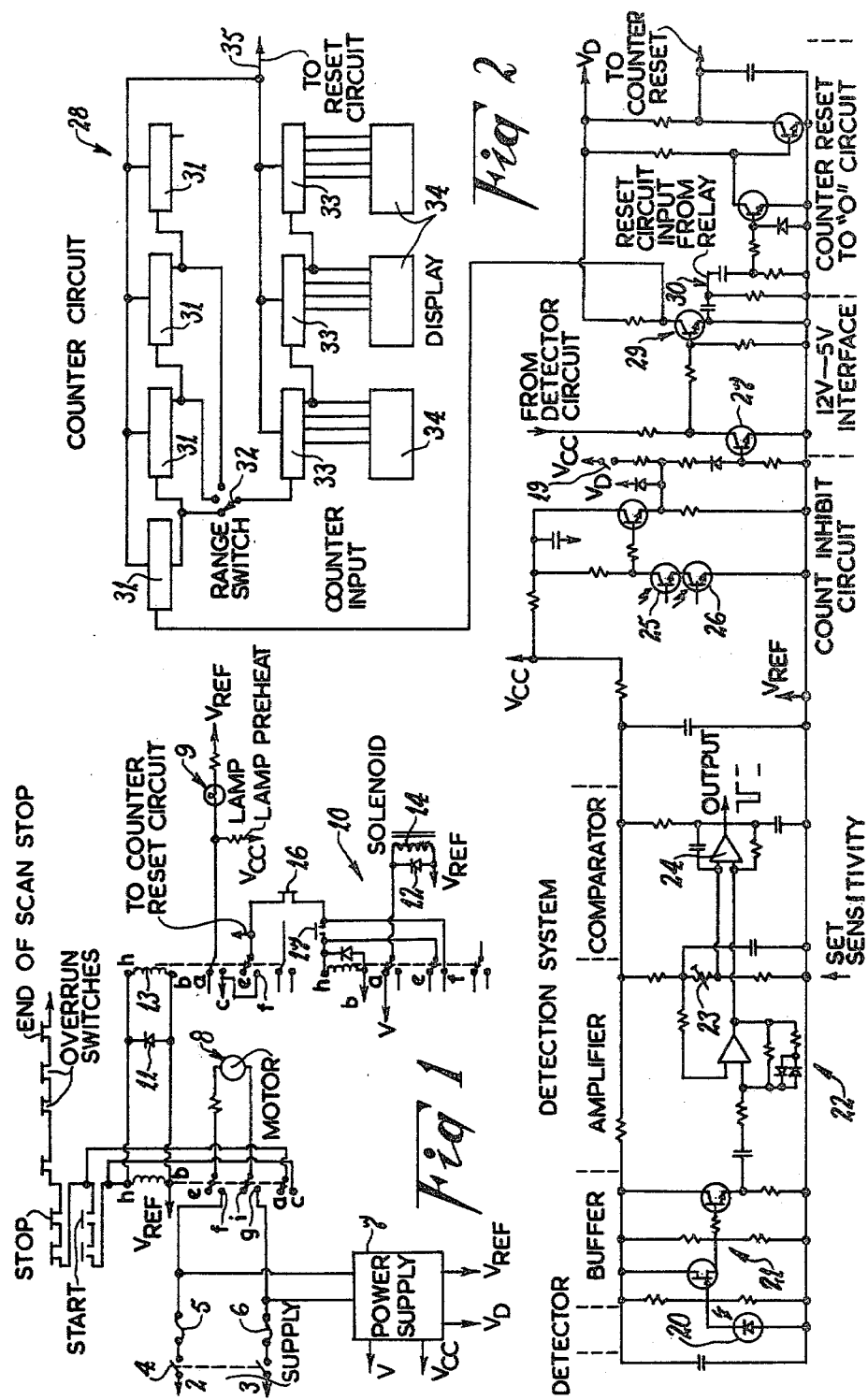

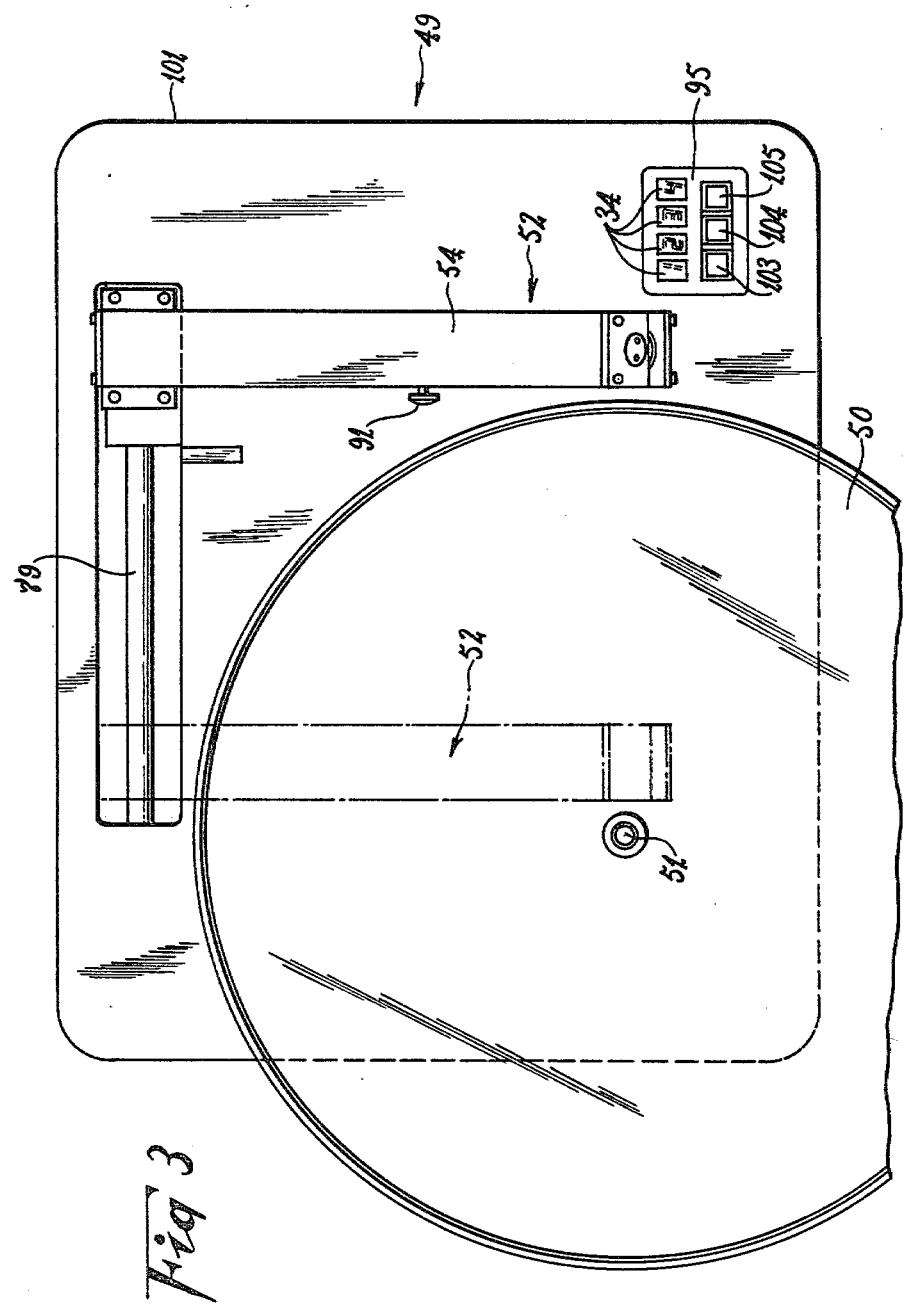

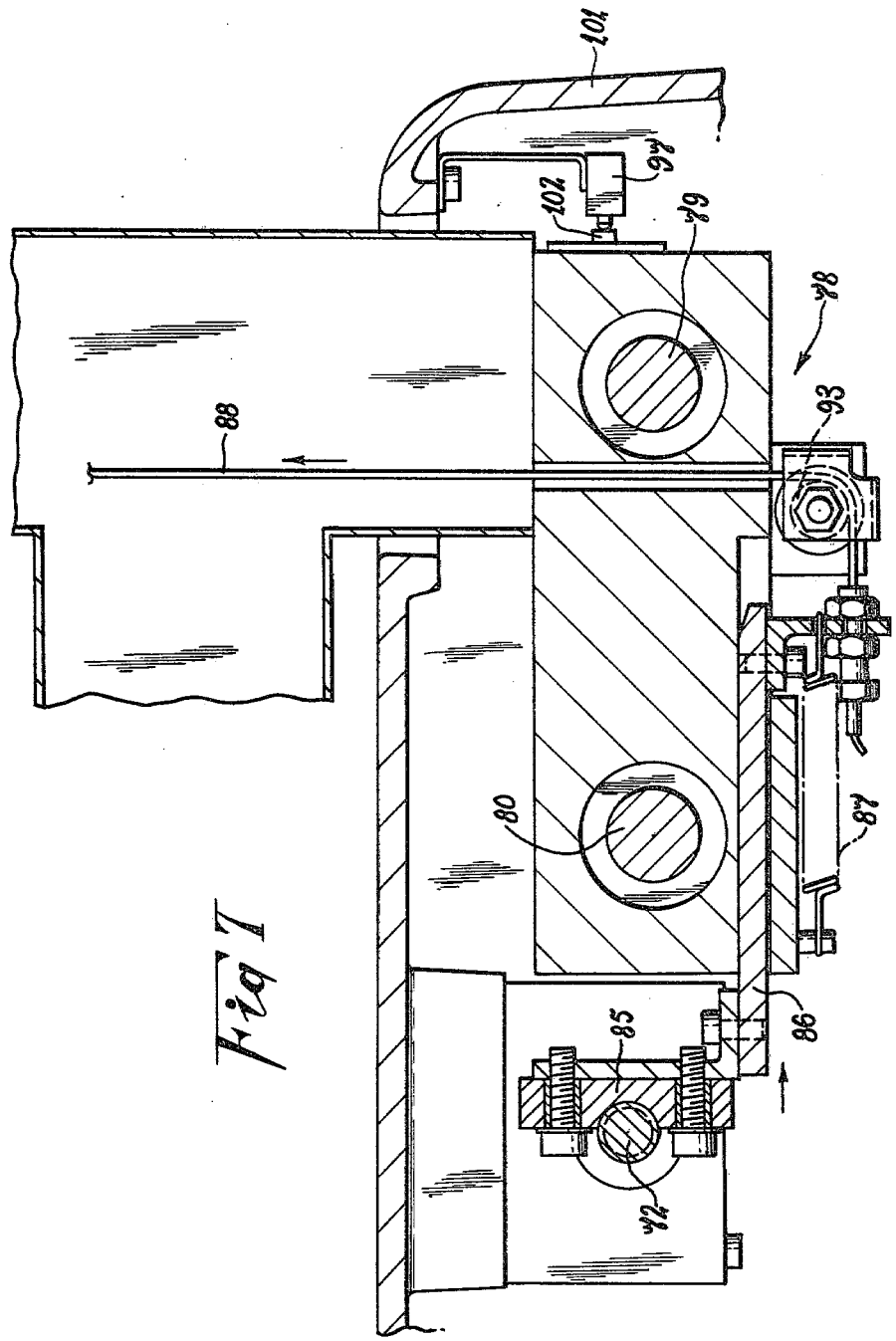

APPARATUS FOR DETERMINING PROPERTIES OF MATTER

This invention relates to a method of and an apparatus for measuring parameters of fibrous or other elongated material.

The invention will be described in relation to determining the above mentioned properties in a root system of a plant. However, it should be understood that the invention is equally applicable to determining the length, and/or diameter of any sample of filaments and/or the number of ends of any sample of branched fibres or filaments and is not limited to this example application.

During research and other investigations it is often necessary or desired to know the total length of root, the range of diameters of the fibres, the number of ends of a plant root system and the age of the root. This information provides an indication of growth performance and other characteristics of the plant. In other arts it is also often necessary to determine the total fibre length, the number of fibre ends or the range of fibre diameters in that sample, such as in a sample of blood.

The only reasonably accurate method of establishing length, diameter and number of ends of a root sample has been to take manual measurements using rulers and calipers for example. This method is both time consuming and tedious. Age has been estimated by judging the colour of the root system.

The object of the present invention is to provide a means for measuring parameters of elongated material such as a root system in which visual counting estimation and measurement is avoided.

In one aspect the present invention provides an apparatus for testing a sample of fibres or filaments including:
a scanning zone in which said sample is located,
scanning means,
transport means for producing relative movement between said scanning zone and said scanning means whereby to define a primary scan path therebetween,
said scanning means including irradiation means arranged to irradiate a portion of said scanning zone, and at least one radiation detector responsive to said irradiation whereby to provide an output indicating the presence or otherwise of a discrete length of fibre or filament in said portion, and
processing means for processing said detector output to provide a measure of one or more parameters of the sample.

In another aspect the invention provides an apparatus for testing a sample of fibres or filaments including:
a scanning zone in which said sample is located,
scanning means,
transport means for producing relative movement between said scanning zone and said scanning means whereby to define a primary scan path therebetween,
said scanning means including a plurality of irradiation devices arranged to irradiate a portion of said scanning zone, and a plurality of radiation detectors responsive to said irradiation, said irradiation devices and said detectors being arranged for relative movement or for selective interrogation whereby to define a secondary scan path, such that movement in said primary scan path will provide an output indicating the presence or otherwise of a discrete length of fibre or filament in said portion and movement or interrogation in said secondary scan path will provide an output representing detail of the fibre or filament in the area surrounding points of intersection of the primary scan path and said discrete lengths of fibre or filament, and
processing means for processing said detector outputs to provide a measure of one or more parameters of the sample.

In another aspect the invention provides an apparatus for determining the root length of a root sample including:
a scanning zone in which said root sample is located,
scanning means,
transport means for producing relative movement between said scanning zone and said scanning means whereby to define a primary scan path therebetween,
said scanning means including irradiation means arranged to irradiate a portion of said scanning zone, and at least one radiation detector responsive to said irradiation whereby to provide an output indicating the presence or otherwise of a discrete length of root in said portion, and
processing means for processing said detector output to provide a measure of the total length of root in the sample.

In another aspect the invention provides an apparatus for determining the number of root ends in a root sample including:
a scanning zone in which said root sample is located,
scanning means,
transport means for producing relative movement between said scanning zone and said scanning means whereby to define a primary scan path therebetween,
said scanning means including a plurality of irradiation devices arranged to irradiate a portion of said scanning zone, and plurality of radiation detectors responsive to said irradiation, said irradiation devices and said detectors being arranged for relative movement or for selective interrogation whereby to define a secondary scan path such that movement in said primary scan path will provide an output indicating the presence or otherwise of a discrete length of root in said portion, and, at each point of intersection of the primary scan path and said discrete length of root, movement or interrogation in said secondary scan path will provide an output indicating the existence of other root lengths within the secondary scan path, and
processing means for processing said detector outputs to provide a measure of the number of branches of root and thus the number of root ends.

In another aspect the invention provides an apparatus for determining the average diameter of roots in a root sample including:
a scanning zone in which said root sample is located,
scanning means,
transport means for producing relative movement between said scanning zone and said scanning means whereby to define a primary scan path therebetween,
said scanning means including a plurality of irradiation devices arranged to irradiate a portion of said scanning zone, and plurality of radiation detectors responsive to said irradiation, said irradiation devices and said detectors being arranged for relative movement or for selective interrogation whereby to define a secondary scan path such that movement in said primary scan path will provide an output indicating the presence or otherwise of a discrete length of root in said portion, and, at each point of intersection of the primary scan path and said discrete lenth of root, movement or interrogation in said secondary scan path will provide an output indicating the minimum distance across said root at said point of intersection, and processing means for processing said detector outputs to provide a measure of root diameter distribution in the root sample.

In another aspect the invention provides an apparatus for testing a root sample including:

a scanning zone in which said root sample is located, scanning means, transport means for producing relative movement between said scanning zone and said scanning means whereby to define a primary scan path therebetween, said scanning means including a plurality of irradiation devices arranged to irradiate a portion of said scanning zone, and plurality of radiation detectors responsive to said irradiation, said irradiation devices and said detectors being arranged for relative movement or for selective interrogation whereby to define a secondary scan path such that movement in said primary scan path will provide an output indicating the presence or otherwise of a discrete length of root in said portion, and, at each point of intersection of the primary scan path and said discrete length of root, movement or interrogation in said secondary scan path will provide an output indicating the existence of other root lengths within the secondary scan path and the minimum distance across said root at said point of intersection, and, processing means for processing said detector outputs to provide a measure of the number of branches of root and thus the number of root ends and of root diameter distribution in the root sample.

In general the apparatus includes a scanning zone in which the fibres to be measured are located. A container for the fibres may be provided. A glass tray or the like has been found suitable for this purpose. The container may rest upon a container support, which, in a preferred form of the invention, is a movable container support. As will be further explained below it may be desired to support chopped sample in a liquid medium. Hence the container may be in the form of a tray for retaining liquid.

The apparatus includes scanning means. The scanning means includes one or more radiation detectors. Each detector advantageously provides an electrical output indicative of the intensity of radiation impinging upon it at any time. The invention will be described with reference to the use of visible radiation (light). However, the invention is not to be taken as limited thereto, since other forms of detectable radiation may be employed. Each detector is prefereably a light sensitive detector such as a photodiode. However, it is to be understood that any other suitable device responsive to radiation may be used. When more than one detector is used the photodiode may be arranged in the form of a matrix or may be in the form of one or more diode arrays. In one form of the invention suitable for determining the diameter of fibres or filaments an array of 256 diodes is present. In the form of the invention suitable for detecting the number of ends in the fibre sample the detectors are preferably arranged in the form of a matrix which may be rotatable either mechanically or rotation may be simulated electronically by sequentially interrogating particular ones of the photodiodes in the array.

The scanning means of the invention may include a radiation source such as an illuminating means for illuminating the fibre sample. If desired, the illuminating means may be located above the support surface so that the radiation reflected by the sample impinges upon the detectors. However, in preference the illuminating means is located beneath the fibre sample so as to illuminate the discrete lengths of root from beneath. When the fibre sample is illuminated from beneath radiation is blocked by the fibres in the sample and shadows are thereby cast. It is possible to detect the presence of this shadow and hence detect the presence of a discrete length of fibre as will be further discussed below. The scanning means may include a lens system for conditioning the radiation. The lens system may include collimating means by which light from the illuminating means may be substantially collimated. In addition, the lens system may include a lens and a reflector for focusing radiation at the or each detector. The reflector may be a light beam splitter for example. The discrete fibre length may be considered as being located at an object plane whilst the or each detector is located at an image plane. If the source used emits coherent radiation, the lens produces a Fourier Transform of the field distribution in the object plane at the image plane at which the detector is located. If a white light source is used a power spectrum of the object plane is produced at the image plane. With the radiation collimated the "focal distance" is a function of refraction and the diffractive limit. Radiation intensity focused at the or each detector is indicative of the absence or presence of a discrete fibre length intersecting that point being scanned. It will be appreciated that, by this preferred means the depth of field is increased.

The scanning means may be arranged to scan the fibre sample in any suitable manner, consistent with the objective of detecting the properties mentioned above. For example, to measure the number of intersections with fibres over a scan path a photodiode matrix, array or a single diode may be employed. When an array or matrix is used for determining the number of intersections only one diode of the array or matrix need be interrogated. For determining diameter or the number of root ends it is advantageous to employ an array or matrix of diodes and to interrogate the diodes in a manner as will be explained below. Whichever property is to be determined the scanning means should be movable relative to the sample to define a scan path.

In one arrangement the relative movement defines a "sawtooth" scan path. This may be achieved by moving the container support in one direction whilst laterally reciprocating the scanning means in a direction perpendicular to the direction of movement of the container support. In a preferred arrangement the relative movement defines a spiral primary scan path. This may be achieved by rotating the container support whilst moving it laterally of the light path. In particular form the primary scan path is achieved by rotating the container support whilst moving the scanning means in a direction radially of the container support.

An embodiment of the invention as applied to measurement of root length will now be described with reference to the accompanying drawings in which:

FIG. 1 is a circuit diagram of a control circuit;

FIG. 2 is a circuit diagram of a data processing circuit;

FIG. 3 is a plan view of root length measurement apparatus;

FIG. 7 is an enlarged section on line VII—VII of FIG. 4.

Figure 4:
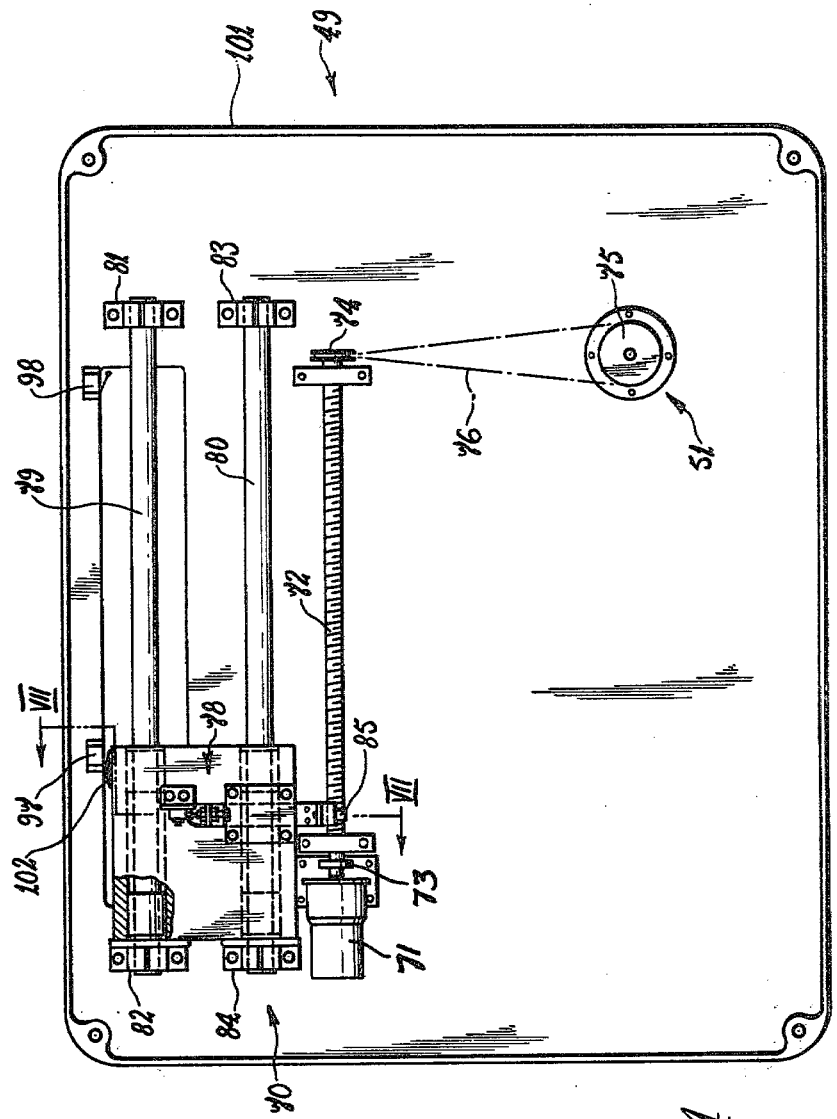
FIG. 4 is an inverted plan view of the apparatus shown in FIG. 3 but with the bottom cover plate removed to show the transport mechanism according to a preferred form of the apparatus.

The apparatus is indicated generally by 49 (see FIGS. 3 to 7).

A radiation transparent container 50 for chopped root is shown supported for rotation about a container support 51. The scanning means is shown generally by the numeral 52. The scanning means comprises first and second spaced apart arms 53, 54 respectively between which the container 50 is located. As is best shown in FIG. 3 the scanning means 52 is adapted for movement between a rest position shown in full lines and an end of scan position shown in broken lines. The scanning means 52 includes lamp 9 mounted in arm 53 and a reflective surface or mirror 56 mounted in arm 54 so that light emitted by the lamp passes through the container and is reflected by the mirror towards detector 57. It should be appreciated that the lamp may alternatively be housed in arm 54 with the mirror 56 and detector 57 housed in arm 53. The lamp 9 conveniently is a quartz-halogen lamp. A condensor lens is shown at 58 and an objective lens at 59. In this way light passing through the container 50 comprises substantially parallel rays. The lens 59 is operative to focus light onto the detector 57. The detector 57 may be located at any convenient location so that light passing through the container 50 may impinge upon it. It is preferred that, to reduce the effects of noise, the detector be located close to the circuit of FIG. 1. A tubular guide 60 may be provided for light reflected by mirror 56. The mirror 56, lenses 58 and 59 together with the lamp 9 form the illuminating means of a preferred form of the invention.

The transport mechanism 70 will be described in relation to FIGS. 4 and 7. A motor 71, with or without suitable reduction gearing drives a lead screw 72 through a coupling 73. The lead screw 72 is suitably journalled at its ends. At the end of the lead screw 72 remote from the motor 71 a pulley 74 is provided attached to the lead screw. A further pulley 75 is attached to the container support 51. A belt 76 operatively couples the pulleys 74 and 75 so that rotation of lead screw 72 causes rotation of the container support which in turn rotates the container 50 on the container support. The arms of the scanning means terminate at an upright arm 77 (FIG. 5), supported at a carriage 78. This carriage is adapted to run along parallel guides 79, 80 which are secured at their respective ends by clamping blocks 81, 82 and 83, 84. A half nut 85 supported by bracket 86 is biased into engagement with the lead screw 72 by spring 87. The half nut 85 may be released from engagement with the lead screw by a release mechanism. The release mechanism (FIGS. 6 and 7) comprises a cable 88 secured at one end to bracket 86, a bell crank 89 to which the other end of cable 88 is secured, a support bracket 90 and an operating button 91. Guides 92, 93 may be provided for the cable 88. When button 91 is pressed, bell crank 89 pivots about pivot 94 to move the cable in the direction of the arrow shown in FIG. 6. This movement causes bracket 86 to be moved against the action of spring 87 and disengages the half nut 85 from the lead screw 72. When the half nut is engaged with the lead screw and the motor is operative the scanning means is driven from the full line position of FIG. 3 to the broken line position of the same figure.

FIG. 3 shows control console 95 which may include such controls as power on and off 103, start 104, stop 105 and manual counter reset if desired together with indicator lights. FIG. 4 shows limit switches 97, 98 which control the supply of power to the motor and hence the movement of the scanning means and container support and reset the counter when the scanning means is returned to its start scan position. The operation of these switches also provides an inhibit signal for the counter means 28 which forms part of the circuit of FIG. 2. The normally closed contacts 16 and the normally open contacts 17 are associated with these limit switches.

Figure 5:
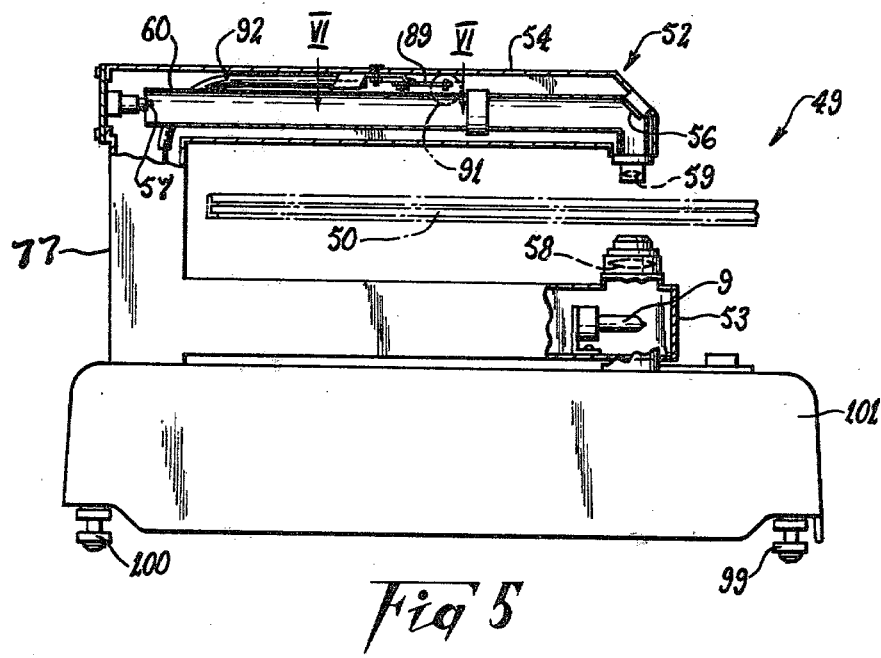
FIG. 5 is a part sectioned side elevation of the apparatus shown in FIG. 3.
Figure 6:
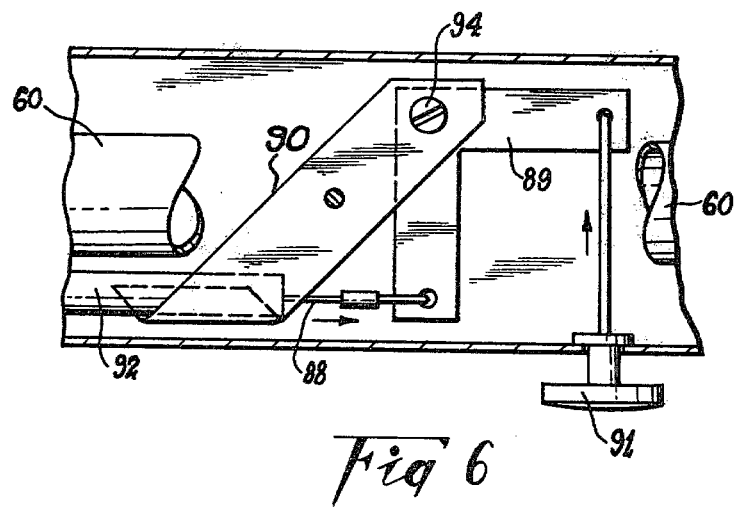
FIG. 6 is an enlarged section on line VI—VI of FIG. 5.

The apparatus shown in FIG. 5 has levelling screw supports, only two of which 99, 100 are visible. A base 101 is shown forming a support and cover for the apparatus.

FIG. 1 shows terminals 2, 3 connectable to an alternating current power supply. A switch 4 may be provided to isolate the supply from the remainder via fuses 5, 6. A suitable powder supply 7, for direct current voltages V, $V_{cc}$ & $V_D$ is provided. The drive motor 8 is provided for driving both the container support and the scanner arms together with control switch gear is shown generally at 8. To provide longer lamp life for the illuminating means the lamp 9 is energized which the motor 8 is operative. A pre-heating circuit is provided for the lamp by essentially connecting the lamp 9 between $V_{cc}$ and a reference potential. A counter reset pulse is provided by the portion of the circuit at 10. Commutation diodes 11, 12 may be provided to minimize problems caused by back emf in the respective solenoids 13, 14. Solenoid 14 together with interlock start switch 15 and normally closed limit switch 16 and normally open limit switch 17 ensure that once the arm has been driven to the end of its scan the operation is not re-startable until the scanner arms are returned to the start of scan position. Like connections in the figure are shown generally with lower case letters. Further control switches as shown may be provided if desired.

FIG. 2 shows a circuit suitable for recording the number intersections with fibres as the detector diode describes the primary scan path. The detector 20 is mounted so that illumination passing through the container impinges upon it. Whenever the beam from the illuminator or lamp 9 is intercepted by a fibre an output is registered at the output terminal of the buffer 21. This buffer is provided to prevent the remainder of the processing circuitry from loading the detector 20.

An amplifier 22 with sensitivity setting means 23 in the amplifier feedback path is provided to control the gain of the amplifier 22. A comparator 24 is provided to provide an output pulse whenever the input thereto exceeds a threshold value.

Photo-transistors 25, 26 may act as end of scan sensors such that when the scanner is at either extreme of its movement path transistor 27 conducts and thus inhibits further inputs being supplied to the counter circuit 28. Switch 19 is a normally open switch and is operative to inhibit the counter. When the scanner is not at these extremes output pulses from comparator 24 are supplied to the base electrode of transistor 29 which, together with the associated biasing components provides an interface between the voltage $V_{cc}$ (12 V for example) and the voltage $V_D$ (5 V for example) supplied to the counter circuit 28. Solenoid 14 switches a reset voltage to terminal 30.

The output from comparator 24, when not inhibited by the inhibit circuit is applied to the counter circuit 28 via the interface portion of the circuit. The counter circuit is provided with a first series of counter elements 31 which may comprise decade counters and a range switch 32. Dependant upon the position of the switch 32, the output from a particular counter element is fed to a second series of similar counter elements 33. In this way a total count of intersections within the ranges 0 to 9.99, 9.99 to 99.9 or 99.9 to 999 may be obtained. It will be appreciated that the output from the counter elements may be in a convenient code such as binary coded decimal. The coded outputs from the elements 33 are shown fed to display units 34 which may include decoder/drivers and seven segment display units or the like.

The reset for the counter circuit at terminal 35 may be provided from the reset circuit where shown in FIG. 2 at terminal 36 or where indicated in FIG. 1.

The operation of the apparatus illustrated is as follows:

With the scanning means in the position shown in full in FIG. 3, the counter 28 in FIG. 2 is reset to zero by depressing an appropriate button on console 95 or as preferred, automatically as described above. Lamp 9 is preheated by the preheat circuit when the apparatus is operative and has power supplied to it. The container 50 is filled with a fibre sample in aqueous suspension. The on button on console 95 is depressed thus initiating the supply of power to the motor 71 and to the lamp 9. With the half-nut 85 in engagement with the lead screw 72 the carriage commences to move towards the broken line position of FIG. 3. Cam 102 operates limit switch 97 initiating the counter 28 when the scanning means has moved past the lip of the container 50. The detector 57 is then operable, in response to discrete lengths of fibre intersecting the beam of light between lenses 58 and 59 to provide outputs indicative of the property being determined. These outputs are registered by the circuit of FIG. 2 and recorded by the counter 28.

At the end of scan position limit switch 98 is operated by cam 102 to inhibit the counter thus preventing it from recording further responses from detector 57 and the circuit of FIG. 1. This occurs because of contacts 16, 17 which function to disconnect power to the motor. The carriage may be returned to the initial position by releasing the half-nut by depressing button 91 and moving it manually to its start position. When power is disconnected from the motor the lamp 9 returns to its preheat condition. After a scan the counter indicates, according to the embodiment illustrated, the total number of times the light beam intersects a length of fibre. Statistically the number of such intersections is proportional linearly to the total length of root in the sample. Thus the apparatus can be calibrated to read out the length of root in the sample under test. Suspension of chopped root in a liquid medium is preferred not only to distribute the root evenly to increase the statistical accuracy but also to prevent drying out of the sample.

Age of a root can be established by its colour. The colour of the root sample can be ascertained by choosing appropriate light emitters and detectors as is known in the art. Thus the apparatus may be calibrated to read out the age of a root sample.

When the scanning means comprises an array or matrix of photodiodes, the primary scan path of the array or matrix is the path of the array or matrix as a whole. However, it is preferred that the array or matrix in itself defines a secondary scan path within the first. To this end when the detectors are in the form of a diode array, the array may be caused to rotate about a selected diode as discussed. The photodiodes provide an output indicative of the presence of a fibre and the number of diodes providing an output at any one point on the primary scan path will vary from a minimum to a maximum during rotation of the array in its secondary scan path. A minimum number of outputs or contrasts is indicative of the array being aligned transverse to a discrete length of fibre whilst a maximum is indicative of an alignment longitudinally of a discrete length of fibre.

It will be appreciated, if the primary scan path is analyzed, that when a fibre is met signals will be emitted by the detectors. The output from the detectors in the secondary scan path are then analysed around the 360 degrees compass. The minimum positive number of contrasts represents the transverse dimension of the fibre, that is to say, indicates the diameter of the fibre.

For the diameter determining aspect the apparatus of the invention further includes data processing means for processing the detector outputs and for sequentially interrogating various detectors. The data processing means includes a memory for storing the detector outputs. From the outputs an indication of the diameter of the root at that point of the scan may be determined and stored.

To determine the diameter of fibres in the sample the operation of the apparatus of the invention is as follows. During a scan by the scanning means a plurality of areas along the scan path may be viewed. For instance, to view or scan a substantially circular area using a diode matrix particular diodes may be interrogated in sequence. The outputs of these diodes being indicative of the presence or absence of a root in the area scanned. In effect, such interrogation is equivalent to having a linear photodiode array rotating with respect to the container support whilst the scanning means describes the primary scan path. In a preferred form a rotating linear diode array is used. When the diode about which the array rotates indicates the presence of a root the remainder of the diodes of the array are interrogated whilst the array rotates. Data processing means detects when a maximum number of diodes provides an output indicative of root presence. This is indicative of the linear array being aligned parallel to a root. The processing means continues to interrogate the diodes after the detection of a maximum until a minimum is detected. Since the diodes of the array are arranged in a linear fashion the number of diode outputs at this minimum is indicative of the diameter of a root since a minimum occurs when the linear array is aligned across a root.

In this way a number of root diameters may be recorded as the scanning means describes a primary scan path across the container. The data processing means stores these diameter readings.

In a further form of this aspect of the invention the detector of the scanning means may comprise two diode arrays arranged perpendicular to each other. These arrays may remain stationary at the scanning means move relative to the container support. The diodes of these two linear arrays are interrogated and when the diode at the point where the two arrays intersect or meet indicates the presence of a root the diodes are further interrogated until two measures, X and Y, across the root are obtained.

The data processor means determines the diameter of the root from the distances X and Y represented by the diode outputs by:

$$\text{Diameter } D = \frac{XY}{\sqrt{X^2 + Y^2}}$$

The numerous diameters so recorded are stored by the processor means preferably in the form of a histogram.

To determine the number of root ends the operation of the apparatus of the invention is as follows. The diode array is caused to rotate about a selected diode of the array. The speed of rotation is much greater than the relative movement between the container support and scanning means such that substantially circular areas along the scan path are viewed. As the array rotates a diode of the array spaced from the selected diode is interrogated during the rotation of the array such that its output is viewed during a substantially circular scan. The number of outputs obtained from this spaced diode may be recorded and analysed. A similar result may be obtained with a stationary matrix of photodiodes that are interrogated to in effect provide a similar result to that afforded by a rotating linear array of photodiodes.

In any event whichever system is adopted the following applies. If there are two outputs during the secondary scan path then what has been met is a single strand. If there are three outputs then a bifurcated junction has been met. If there are four outputs then what has been met is a cross over of two strands. For higher numbers of outputs even numbers are divided by two and if the resultant is an odd number, a bifurcated junction is recorded. Odd numbers of outputs are recorded as a bifurcated junction. In this way, using this algorithm, the number of root junctions detected in the primary scan path of the scanning means may be recognized.

In the end determination aspect of the invention the apparatus also includes data processing means which receives data indicative of the outputs of the photodiodes and performs a calculation using the above mentioned algorithm to determine whether the number of outputs from the spaced diode in the secondary scan path are indicative of a junction or a cross-over. The data processing means in this aspect may provide an output each time a junction is recognised. Alternatively, the data processing means may summate the number of junctions detected and provide an output indicative of the total. The data processing means in this aspect includes data storage and control means. Advantageously the data processing means may be in the form of a central processing unit. Preferably a dedicated device is used.

In order to operate the apparatus of the invention the root sample may be prepared by dividing the roots, cutting them into discrete lengths and randomly placing them in aqueous suspension, in the container. It is preferred to suspend the sample in an aqueous solution since this maintains the integrity of the sample and therefore more accurate results may be obtained.

In the end detection aspect if a stationary linear diode array aligned transversely of the scan path is used the diodes of the array may be interrogated during a scan path such that a series of substantially square or rectangular areas are scanned. An area scanned may be defined by, at the start of the scan, interrogating all of the diodes of the array and at the end of the area by similarly interrogating all the diodes, whilst in between these end positions only interrogating two diodes of the array; one located at each end thereof. In this way the number of discrete lengths of fibre crossing the sides of the scan area at that point is equivalent to a number of contrasts or outputs as previously mentioned.

A similar result may be achieved with a diode matrix. In this case the matrix itself defines an instantaneous scan area which may be of any desired shape depending upon which diodes are interrogated.

The area of scan of the detectors in the case of a diode matrix or stationary linear diode array may be controlled by only interrogating a limited number of the diodes. For a rotating linear array the area scanned may be controlled by interrogating a diode spaced a particular distance from the selected diode. If the sample at the area scanned by the detector comprises roots of small diameter or large diameter the area of the scan at that point may be adjusted accordingly.

Errors may occur in that the orientation and spatial arrangement of the fibre sample may be such that a junction is recognised when in fact none exists in the secondary scan path. For example where the random orientation is such that two discrete lengths of fibre that are substantially parallel to one another have a third length of fibre crossing over them, the spaced diode in the rotating linear array will provide outputs which, when analysed, indicate the presence of a junction. Such errors may be statistically dealt with. Further the occurrence of errors is minimized by limiting the area described during the secondary scan path commensute with the diameter of the sample at that point.

The data processing means stores and summates information indicative of the number of junctions detected to provide a count of the total number of junctions in the sample as mentioned above. In addition the data processing means interrogates the diodes of the detector and limits the number of diodes interrogated in dependance upon the diameter of the sample at that part of the scan so as to limit the area scanned by the detector.

For the length determination aspect of the invention the data processing means includes signals shaping means for providing an output indicative of the presence of a discrete length of fibre at a location during a scan of the scanning means. Preferably the pulse shaping means is a comparator which provides a pulse output when the detector output exceeds a threshold value. In addition the processing means may include a sensitivity setting means for varying the threshold at which the radiation impinging upon the detector is recognized as indicating the presence of a discrete length of fibre. The sensitivity setting means may be interposed between the signal shaping means and the detector. Advantageously the sensitivity setting means consists of an amplifier having a variable circuit element in its feedback path so that the game of the amplifier may be altered. The processing means may also include a buffer interposed between the detector and the sensitivity setting means to reduce loading on the detector. The buffer may comprise a voltage follower in the form of an operational amplifier. Advantageously the buffer may comprise a field effect transistor (FET) connected as a voltage follower; the FET having its control electrode connected to the detector output.

The processing means for the length measurement aspect preferably includes a counter means for counting the number of pulses occurring at the output of the pulse shaper.

The counter means may be adapted to provide, at its output, an indication of the total count of pulses over a fixed range of values. In this form the counter means preferably comprises a series of decade counter elements each adapted to provide at its output an indication of a portion of the total count; each count corresponding to a progressively increasing power of ten.

In a preferred form the counter means includes means for changing the range of the total count. In this form the counter means includes a first series of decade counter elements having their outputs coupled to a range changing switch and a second series of decade counter elements which provides at their outputs an indication of the total count. The range switch being adapted to connect different ones of the first series of decade counter elements to the input of the second series such that the second series of decade counter elements may provide outputs indicative of different ranges such as from 0 to 9.99, 99.9 to 999 or any other convenient ranges.

The counter means in either of its forms preferably also includes reset means to enable the count to be recommenced for subsequent new scans of a sample.

The processing means may further include an interface circuit for scaling the pulse output from the pulse shaper to make it compatible with the pulse magnitude suitable for the counter means. The interface circuit may be of any suitable means but preferably comprises a divider network having its output coupled to a bistable element; the output of the bistable element being directly coupled to input of the counter means.

Advantageously, the processing means further includes count inhibit means which enable the pulse output from the pulse shaper to be disconnected from the counter means should the scanner means be outside the scanning zone. Preferably the inhibit means comprises means for connecting the pulse output from the signal shaper means to a reference potential such as ground instead of to the interface means when the scanner means is outside the scanning zone. The inhibit means may include one or more sensors which provide an output when the scanner means moves outside the scanning zone. Advantageously the sensor output is operative to switch a bi-stable element to disconnect the pulse output from the interface means. The sensor may comprise two photo transistors having their conduction paths in series; one of said transistors being connected to the control electrode of the bi-stable element. In response to the light impinging upon the photo transistors being cut the pulse output is connected to ground potential.

The inhibit means defines the zone to be scanned and avoids the possibility of counting the edge of the container.

The apparatus preferably includes output indicating means. The indicating means is connected to the output of the counter means and provides a visual indication of the total count of the pulse output. The output indicating means may be of any convenient form. For example, the output indicating means may comprise a diode segment display or liquid crystal display or a series of tumbler wheels which rotate in response to the counter means output or any other suitable means.

I claim:

1. Apparatus for scanning and measuring physical characteristics of a plant root sample comprising a scanning zone in which the root sample, which has been cut indiscriminantly into discrete lengths, may be uniformly distributed and randomly orientated; scanning means; transport means for producing relative movement between said scanning zone and said scanning means, said transport means defining a substantially spiral primary scan path between said scanning zone and said scanning means, said scanning means including at least one irradiation means arranged to irradiate a portion of said scanning zone, and at least one radiation detector responsive to the irradiation from said irradiation means for producing an output indicating the presence or otherwise of a discrete length of root in said portion; and processing means for processing the output of said detector to provide a measure of at least one characteristic of the sample.

2. Apparatus as in claim 1 wherein the detected presence of discrete lengths of root along the primary scan path provides a measure of the total length of root in the sample.

3. Apparatus as in claim 1 wherein said scanning means includes a plurality of irradiation means arranged to irradiate the portion of said scanning zone and a plurality of radiation detectors responsive to said irradiation, the plurality of means being arranged for relative movement or selective interrogation whereby to define a secondary scan path such that movement in said primary scan path will provide an output indicating the presence or otherwise of a discrete length of root in said portion and movement or interrogation in said secondary scan path will provide an output representing detail of the roots in the area surrounding points of intersection of the primary scan path and said discrete lengths of said root sample and said processing means processes said outputs to provide a measure of at least one parameter of the sample.

4. Apparatus as in claim 3 wherein movement or interrogation in the secondary scan path may provide outputs representing the presence of at least one discrete root length in the area of the secondary scan path and said processing means processes said detector outputs to provide a measure of the number of branches of root and thus the number of root ends.

5. Apparatus as in claim 3 wherein movement or interrogation in said secondary scan path provides an output indicating the minimum distance across discrete lengths of root at said point of intersection and said processing means provides a measure of root diameter distribution in the root sample.

6. Apparatus as in any one of claims 2 to 5, wherein said irradiation means irradiate light of at least one color, whereby said detectors provide outputs indicative also of color and thereby age of the root sample.

7. Apparatus as in any one of claims 3 to 5, wherein said irradiation means is in the form of a diode array rotatable to define said secondary scan path.

8. Apparatus as claimed in any one of the claims 3 to 5, wherein said detectors are in the form of a matrix selectively interrogated thereby to define said secondary scan path.

9. Apparatus as claimed in any one of claims 1 to 5, wherein said transport means includes drive means to rotate said container while said scanning means is moved linearly thereby to define said spiral scan path.

* * * * *